(12) United States Patent
Gilliam et al.

(10) Patent No.: US 10,058,889 B2
(45) Date of Patent: Aug. 28, 2018

(54) WEAR RESISTANT AND BIOCOMPATIBLE COATINGS FOR MEDICAL DEVICES AND METHOD OF FABRICATION

(71) Applicant: Kettering University, Flint, MI (US)

(72) Inventors: Mary Gilliam, Brighton, MI (US); Susan Farhat, Holt, MI (US); Ali Zand, East Lansing, MI (US)

(73) Assignee: Kettering University, Flint, MI (US)

( * ) Notice: Subject to any disclaimer, the term of this patent is extended or adjusted under 35 U.S.C. 154(b) by 35 days.

(21) Appl. No.: 14/774,318

(22) PCT Filed: Mar. 10, 2014

(86) PCT No.: PCT/US2014/022505
§ 371 (c)(1),
(2) Date: Sep. 10, 2015

(87) PCT Pub. No.: WO2014/164469
PCT Pub. Date: Oct. 9, 2014

(65) Prior Publication Data
US 2016/0023240 A1    Jan. 28, 2016

Related U.S. Application Data

(60) Provisional application No. 61/775,797, filed on Mar. 11, 2013.

(51) Int. Cl.
*B05D 1/00* (2006.01)
*B05D 3/14* (2006.01)
(Continued)

(52) U.S. Cl.
CPC ............. *B05D 1/62* (2013.01); *A61L 27/16* (2013.01); *A61L 27/34* (2013.01); *A61L 31/10* (2013.01);
(Continued)

(58) Field of Classification Search
None
See application file for complete search history.

(56) References Cited

U.S. PATENT DOCUMENTS 6,013,855 A  * 1/2000  McPherson ............. A61L 27/34
                                                  427/2.24
7,608,839 B2   10/2009  Coulombe et al.
(Continued)

FOREIGN PATENT DOCUMENTS

WO       2008/060522 A2    5/2008
WO    WO-2008060522 A2  *  5/2008  ............... B05D 1/62

OTHER PUBLICATIONS

European Patent Office, Rijswijk, Netherlands, International Search Report of International Application No. PCT/US2014/022505, dated Jun. 24, 2014, 3 pages.

*Primary Examiner* — Cachet I Sellman
(74) *Attorney, Agent, or Firm* — Brinks Gilson & Lione (57) ABSTRACT

A method of forming a biocompatible or biologically inert article for use in an application in which the article will make contact with at least one tissue, organ, or fluid within a human or animal body is provided. The method generally comprises providing an article having an external surface; selecting chemical precursors; using a means to direct one or more chemical precursors towards or to apply such chemical precursors to the external surface; activating the chemical precursors by exposing said precursors to atmospheric pressure plasma; and grafting and/or cross-linking the chemical precursors to form a solid coating adjacent to the external surface of the article.

12 Claims, 8 Drawing Sheets

(51) Int. Cl.
  *A61L 27/16* (2006.01)
  *A61L 27/34* (2006.01)
  *C08L 33/12* (2006.01)
  *A61L 31/10* (2006.01)
  *B05D 1/02* (2006.01)

(52) U.S. Cl.
  CPC .............. *B05D 1/02* (2013.01); *B05D 3/144* (2013.01); *B05D 3/147* (2013.01); *B05D 3/148* (2013.01); *C08L 33/12* (2013.01); *A61L 2420/02* (2013.01)

(56) References Cited

U.S. PATENT DOCUMENTS

| | | |
|---|---|---|
| 8,178,168 B2 | 5/2012 | O'Neill et al. |
| 8,426,199 B2 | 4/2013 | Zimmermann |
| 2003/0175408 A1* | 9/2003 | Timm .................. A61L 2/14 427/2.1 |
| 2007/0087131 A1* | 4/2007 | Hutchinson .............. C08J 7/123 427/533 |
| 2007/0093076 A1* | 4/2007 | Mikhael .................. B05D 1/60 438/780 |
| 2010/0035074 A1 | 2/2010 | Cohen et al. |
| 2010/0203339 A1 | 8/2010 | Eryilmaz et al. |
| 2010/0255053 A1 | 10/2010 | Savage-Erickson |
| 2010/0317080 A1 | 12/2010 | Zimmermann et al. |
| 2011/0008407 A1 | 1/2011 | Gan et al. |
| 2011/0189493 A1 | 8/2011 | Ott et al. |
| 2012/0171354 A1* | 7/2012 | O'Neill .................. A61L 27/34 427/2.25 |
| 2012/0321776 A1* | 12/2012 | Vetrecin .................. B05D 3/147 427/2.1 |

* cited by examiner

| Pre-treat | Input Power (W) | Scan Speed (m/min) | Initial Adhesion |
|---|---|---|---|
| yes | 945 | 20 | pass |
| no | 965 | 20 | fail |
| yes | 1330 | 10 | pass |
| no | 1370 | 10 | pass |
| yes | 1250 | 15 | pass |
| no | 1330 | 15 | pass |
| yes | 1250 | 20 | pass |
| no | 1350 | 20 | fail |
| yes | 960 | 10 | pass |
| no | 965 | 10 | fail |
| yes | 980 | 15 | pass |
| no | 985 | 15 | pass |

Figure 8

| Plasma Power (W) | Scan Speed (m/min) | Thickness (μm) | Stand. Dev. (μm) |
|---|---|---|---|
| 950 | 10 | 2.00 | 0.06 |
| 1250 | 10 | 2.23 | 0.08 |
| 1250 | 20 | 1.35 | 0.11 |

| PEI Concentration | Input Power (W) | Scan Speed (m/min) | Adhesion |
| --- | --- | --- | --- |
| 2 wt.% in H2O | 1375 | 10 | pass |
| | 950 | 10 | fail |
| | 945 | 10 | fail |
| | 1150 | 10 | pass |
| 4 wt.% in H2O | 1400 | 10 | pass |
| | 900 | 10 | fail |
| | 950 | 10 | fail |
| | 1200 | 10 | pass |

Figure 11

WEAR RESISTANT AND BIOCOMPATIBLE COATINGS FOR MEDICAL DEVICES AND METHOD OF FABRICATION

CROSS REFERENCE TO RELATED APPLICATIONS

This application is the National Stage of International Application Serial No. PCT/US2014/022505 filed on Mar. 10, 2014, designating the United States and published in English, which claims the benefit of the filing date under 35 U.S.C. § 119(e) of U.S. Provisional Application No. 61/775,797 filed Mar. 11, 2013, the entire contents of each of which are hereby incorporated herein by reference.

This disclosure relates generally to coatings for articles such as medical devices, especially artificial implants and other devices fabricated for use inside the body, and the methods of preparing the coatings. More specifically, this disclosure relates to durable grafted coatings, which are biocompatible, resistant to wear, and can prevent the release into the body of any bulk material from which the articles are made.

The statements in this section merely provide background information related to the present disclosure and may not constitute prior art. Medical devices and biomedical implants may be fabricated from metal, ceramic, plastics, or a combination. Medical devices used inside the body, such as artificial implants, can release particles into the body due to wear or erosion, resulting in the release of immunogenic substances. The release of such particles may cause infection, inflammation, destruction of bone and muscle, or other negative effects on the body. For example, after total hip replacement surgery using a metal-on-plastic artificial implant, periprosthetic osteolysis (bone loss in the vicinity of the replacement joint) constitutes one of the most recurring complications leading to reduced lifetimes for these implants. Other materials used in artificial implants, including ceramic or metal-on-metal parts, have their own inherent disadvantages. The problem with metal-on-metal parts is the release of small metal particles into the body which can cause inflammation and also infection if passed into the bloodstream. Ceramic implants possess higher resistance to wear than metal implants; however, the brittle nature of ceramics increases the risk of fracture or breakage. Such problems with artificial implants can cause premature failure, requiring a replacement revision surgery, which is not always as successful as the original surgery and presents additional high risks for the elderly.

The biological fluids that coat the surface of the hip joint do not sufficiently wet the surface, leading to increased friction and ultimately the release of wear particles. This is due to the hydrophobic nature of HMWPE in aqueous biological fluids. Wear particles generated cause an immune response and result in macrophages that release proteolytic enzymes that will not only destroy the wear particles but also result in the erosion of bone in the vicinity of the prosthesis. Current research has been dedicated to grafting surface functional groups and hydrophilic, biocompatible polymers to the HMWPE surface to create a wettable surface, thereby reducing the abrasion and formation of wear particles. The grafted polymers must be not only biocompatible, but must also be uniformly deposited onto the surface of the implant and be strong enough to withstand friction-resulting movement expected during usage.

Surface attachment of polymers has been accomplished by various methods including chemical or radiation based free-radical or ionic grafting, photochemical grafting, plasma induced grafting and enzymatic grafting. Some of the photochemical and radiation based techniques are time intensive, and often the attachment of the polymer to the substrate is difficult to achieve uniformly. Plasma treatment, on the other hand, utilizes high-energy, ionized species (or excited state species) to create active sites on the surface of the substrate necessary for grafting of chemicals. Exposure of the liquid polymer/monomer solution to the active sites on the surface results in the formation of chemical bonds.

Plasma assisted polymerization has been established previously. For example, a multi-step process in U.S. Pat. No. 8,178,168 uses plasma treatment of a free radical initiated polymerisable monomer solution with soft ionization plasma to prevent defragmentation of the polymer before depositing to a substrate, leaving the coated substrate with the same features as that of the bulk polymer. U.S. Publication No. 2010/00350741 presents a method of graft polymerization with atmospheric pressure plasma to covalently bond polymers to silicone substrates using a multi-step process of surface activation and exposure to a humidity chamber before grafting. Atmospheric pressure has been known to offer an advantage over vacuum plasma due to its ease of in-line processing, lower maintenance costs, and faster processing times.

Additionally, plasma methods have been employed to improve surfaces for biomedical applications. U.S. Pat. No. 7,608,839 shows a method of using atmospheric pressure plasma for applications such as detachment of cells or skin treatments. U.S. Pat. No. 8,426,199 includes a method for improving biocompatibility of surfaces using various plasma treatments including microwave or atmospheric pressure. U.S. Publication No. 2010/0203339 presents a method of depositing carbon based films to decrease friction and improve wear properties for steel substrates.

Attaching various polymers or other chemical agents to substrates using plasma methods and/or wet chemical techniques has been shown to be successful for various applications. The method described in U.S. Publication No. 2010/0255053 can be used to produce porous scaffolds for medical devices with bioactive compounds applied using plasma or other spraying techniques. In U.S. Publication No. 2011/0008407, both osseointegration and antimicrobial agents were integrated to various substrates to improve bone growth and eliminate infection. U.S. Publication No. 2011/0189493 presents a method to crosslink Si containing molecules with plasma polymerization in order to improve biocompatibility. Plasma assisted spraying techniques shown in U.S. Publication No. 2012/0171354 result in attachment of materials including biomolecules and living cells to substrates, such as metals to improve bone fixation for medical implants.

The examples in the related art fall short in accomplishing wear resistance as well as biocompatibility that is necessary for articles fabricated for use in a human or animal body.

BRIEF SUMMARY OF THE INVENTION

The present disclosure provides coatings for articles that are fabricated for use inside a human or other animal body, such as biomedical implants and other medical devices. The articles may be made from any metallic, ceramic, or plastic material, including any combination thereof. The method of coating includes activation of chemical precursors using atmospheric pressure plasma and subsequent surface grafting and cross-linking of monomeric and polymeric molecules to form a solid coating. Optionally, a sub-layer can be applied to the article to provide additional functionality.

Alternatively, the surface of the article or the surface of the optional sub-layer may pre-treated before application of the coating.

The chemical precursors for use in coating the articles may comprise polymers, monomers, other small molecules, or mixtures thereof. The chemical precursors may be dissolved in water or other solvents. According to one aspect of the present disclosure, the chemical precursors contain a polymer or monomer that has demonstrated biocompatibility and biological inertness. The chemical precursors may also include other chemicals that provide alternate functionality to the coating, such as increased wear resistance, cross-linking, or hydrophilicity, as well as any other physical or chemical function desired for a specific application.

The chemical precursors are activated by atmospheric pressure plasma, which partially dissociates the chemical precursors, grafts the chemical precursors to the surface of the article, and cross-links the chemical precursors to form the coating. According to one aspect of the present disclosure, the chemical precursor is delivered to the surface of the article simultaneously as the atmospheric pressure plasma is directed towards the surface of the article. The chemical precursor may be delivered by any form of an atomization or a spray process that uses nitrogen, air, noble gas, or a combination of said gases capable of transporting the chemical precursors. In yet another aspect of the present disclosure, the chemical precursors are vaporized before directed to the surface of the article. The chemical precursors can also be applied to the entire surface of the article by dip coating, flow coating, spray coating, or spin coating prior to exposure to plasma for activation and cross-linking.

At the same time as delivery of the precursors or subsequent thereto, atmospheric pressure plasma is directed towards the surface of the article, which activates the chemical precursor by partial molecular dissociation, followed by surface grafting and/or cross-linking of the activated precursor molecules to form a solid coating. The atmospheric pressure plasma may be generated by any feasible method of generating plasma under atmospheric conditions, such as electrical ignition using direct current (DC), alternating current (AC), or pulsed current, among others. The type of plasma source selected can include, but is not limited to, Dielectric Barrier Discharge (DBD), microwave plasma systems, hollow cathode systems, various plasma jets, and plasma arrays.

According to another aspect of the present disclosure, a sub-layer is applied to the article to provide additional functionality to the article. An example of such a sub-layer is a ceramic or tribological layer to provide additional wear and abrasion resistance and/or to increase adhesion of the article to coating. This sub-layer may applied by any means known to one skilled in the art, including physical vapor deposition, chemical vapor deposition, or plasma enhanced chemical vapor deposition.

When desirable, the surface of the article may be chemically modified with a pre-treatment before application of the coating. The method of pretreatment may be selected from any means known to one skilled in the art, including, but not limited to, plasma and corona treatment, chemical etching, priming with other chemicals, applying an adhesive film, and/or physical abrasion. Alternatively, the surface pre-treatment is performed using atmospheric pressure plasma exposure.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIGS. 5A-5E are Fourier Transform Infrared Spectroscopy (FTIR) spectra showing measurements obtained from untreated high molecular weight polyethylene (HMWPE) and plasma coatings using the precursors poly(2-hydroxyethyl methacrylate) (PHEMA), hydroxyethylmethacrylate (HEMA), polyethylenimine (PEI), and polyethylene glycol (PEG);

FIGS. 6A-6D are FTIR spectra that show a comparison of the grafted surfaces corresponding to those plots shown in FIGS. 5B-5E with the bulk form of each polymer;

DETAILED DESCRIPTION

The following description is merely exemplary in nature and is in no way intended to limit the present disclosure or its application or uses. It should be understood that throughout the description, corresponding reference numerals indicate like or corresponding parts and features.

The present disclosure generally relates to a coating for use in articles, such as biomedical implants or medical devices, which makes contact with tissues and fluids inside a living body, especially those that may release particles into the body due to motion and/or erosion. The present disclosure also relates to a method of applying said coating to the surface of the articles in preparation of these articles being implanted or used within the body.

According to one aspect of the present disclosure, the composition of the coating is derived from polymeric and monomeric chemical precursors that are biocompatible, biologically inert, and/or generally inhibit immune response inside the body. The method of activation of the chemical precursors includes atmospheric pressure plasma, which partially dissociates the chemical precursors and subsequently grafts the chemical precursors to the surface of the article and cross-links the activated chemical precursors to form a solid, durable coating. Alternatively, a sub-layer may be applied to the surface of the article prior to application of the coating in order to provide additional functionality, such as increased hardness and resistance to wear. Alternatively, the surface of the article may be chemically modified with a pre-treatment before coating.

The article or substrate upon whose surface the coating is applied may include any device that is fabricated for use as a biomedical implant, medical device, or other object that is inserted into or contacts the tissue, organs, or fluids present inside the body of a human or animal. The choice of the material of construction for such an article or substrate may include any material selected as one from the group of metal, ceramic, plastic, and combination thereof.

The coating is composed of chemical precursors that are biocompatible and/or biologically inert. The chemical precursors may consist of polymeric materials, monomeric materials, or a combination thereof. The polymeric materials may include, but not be limited to, one or more of polymethacrylates, polyacrylates, polyurethanes, polyethylene, polyanhydrides, polyesters, polyglycolic acid, polylactic acids, polycaprolactone, and polyketones. Alternatively, the polymeric materials may include polyhydroxyethylmethacrylate (pHEMA), polyethylenimine (PEI), polyvinyl alcohol, polyethylene glycol (PEG), or polyvinyl pyrolidone. Alternatively, the polymeric materials may include any polymer approved by the Federal Drug Administration (FDA) for use in the human body.

Monomers or small molecules may be used individually as coating precursors or they may also be used in conjunction with polymeric materials in order to provide increased cross-link density and/or add other functional groups and properties to the coatings. Alternatively, other molecules, including but not limited to oligomers, may be added to the coating precursors. These other molecules are independently selected to provide additional functionality to the coating based on a desired function or property. The coating precursor or mixture of precursors is selected to provide the level of wear resistance, cross-link density, biocompatibility, and other properties of the coating based on the substrate material and final intended application of the article.

According to another aspect of the present disclosure, the coating precursor may be initially in a liquid phase or a vapor phase prior to being applied to the surface of the article. If the precursor exists in a solid phase under atmospheric pressure and temperature, the solid may be dissolved in a solution of water, monomer, other solvent, or a combination thereof.

The coating precursor is delivered to the surface of the article by any means of flow, dip, spray, atomization, or vapor delivery known to one skilled in the art. In one example of such an application process, a flow of a carrier gas can be directed to the surface of the article. The chemical precursor is allowed to enter or be injected or drawn into this gas stream. In this specific case, the carrier gas for the chemical precursor delivery may be any gas that does not form a solid coating, such as nitrogen, oxygen, noble gases, carbon dioxide, or any combination thereof. The flow rate of the chemical precursors, flow rate of the carrier gas, and flow exit location may be tailored based on the substrate material and final application of the article. Simultaneous to chemical precursor delivery, plasma arising from a plasma generator can be directed towards the surface of article. The surface of the article is thus exposed to atmospheric pressure plasma for the creation of reactive sites, while the precursor is activated by partial dissociation, followed by surface grafting and cross-linking. In another method, a liquid precursor can be injected directly into the plasma exiting the plasma generator.

Figure 1:
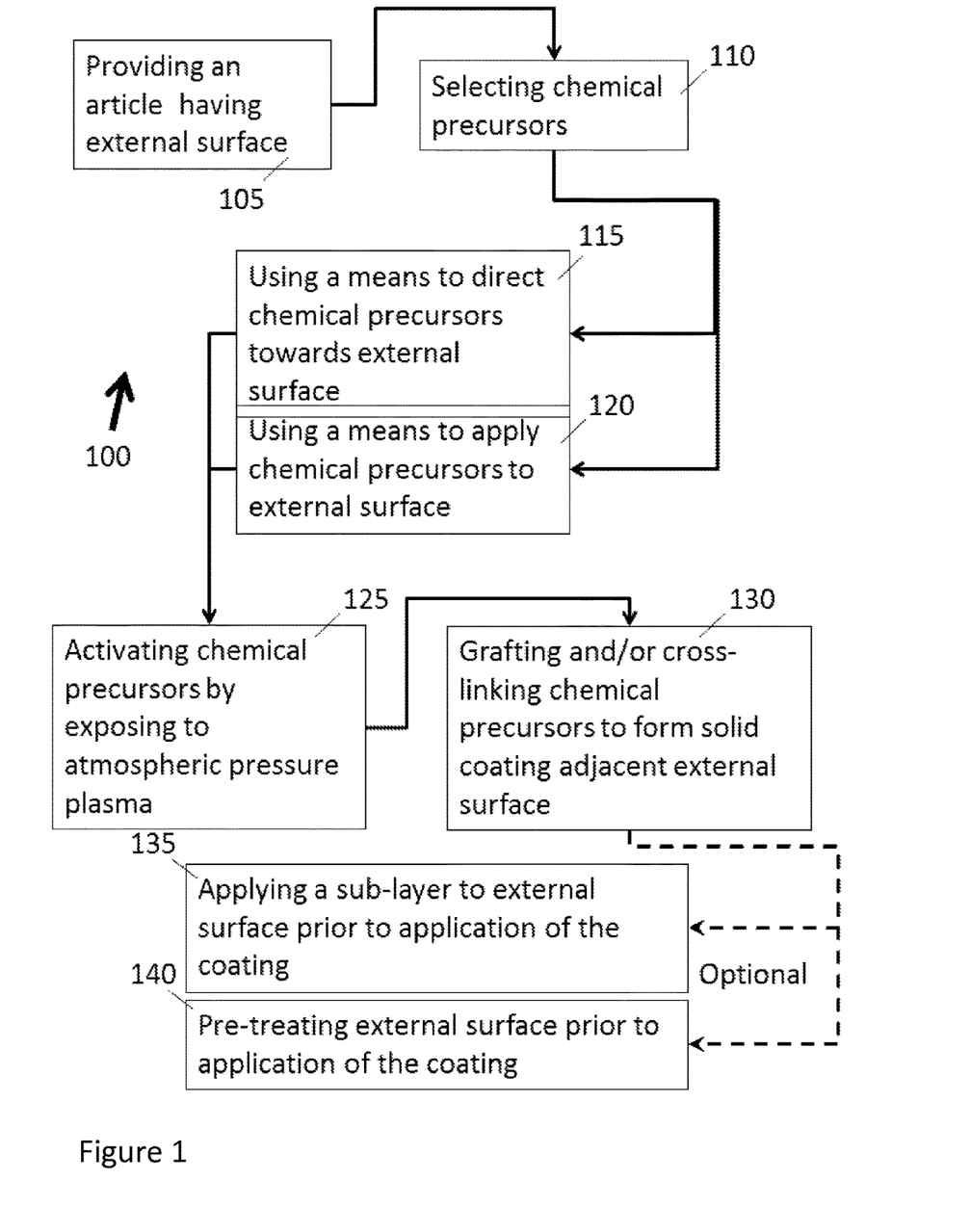
FIG. 1 is a schematic representation of a process or method used to form an article having a protective coating according to the teachings of the present disclosure.

Referring to FIG. 1, the method 100 may be generally described as comprising the steps of providing 105 an article having an external surface; selecting 110 chemical precursors; using a means to direct 115 one or more chemical precursors towards or to apply 120 such chemical precursors to the external surface; activating the chemical precursors 125 by exposing said precursors to atmospheric pressure plasma; and grafting and/or cross-linking the chemical precursors 130 to form a solid coating adjacent to the external surface of the article. Optionally, the method 100 may further comprise the step of applying a sub-layer 135 to the external surface of the article or pre-treating 140 the external surface prior to the application of the solid coating. In this case, the sub-layer or the pretreatment is capable of enhancing adhesion of the solid coating to the article, providing additional wear or abrasion resistance, or increasing hardness of the coating.

Figure 2:
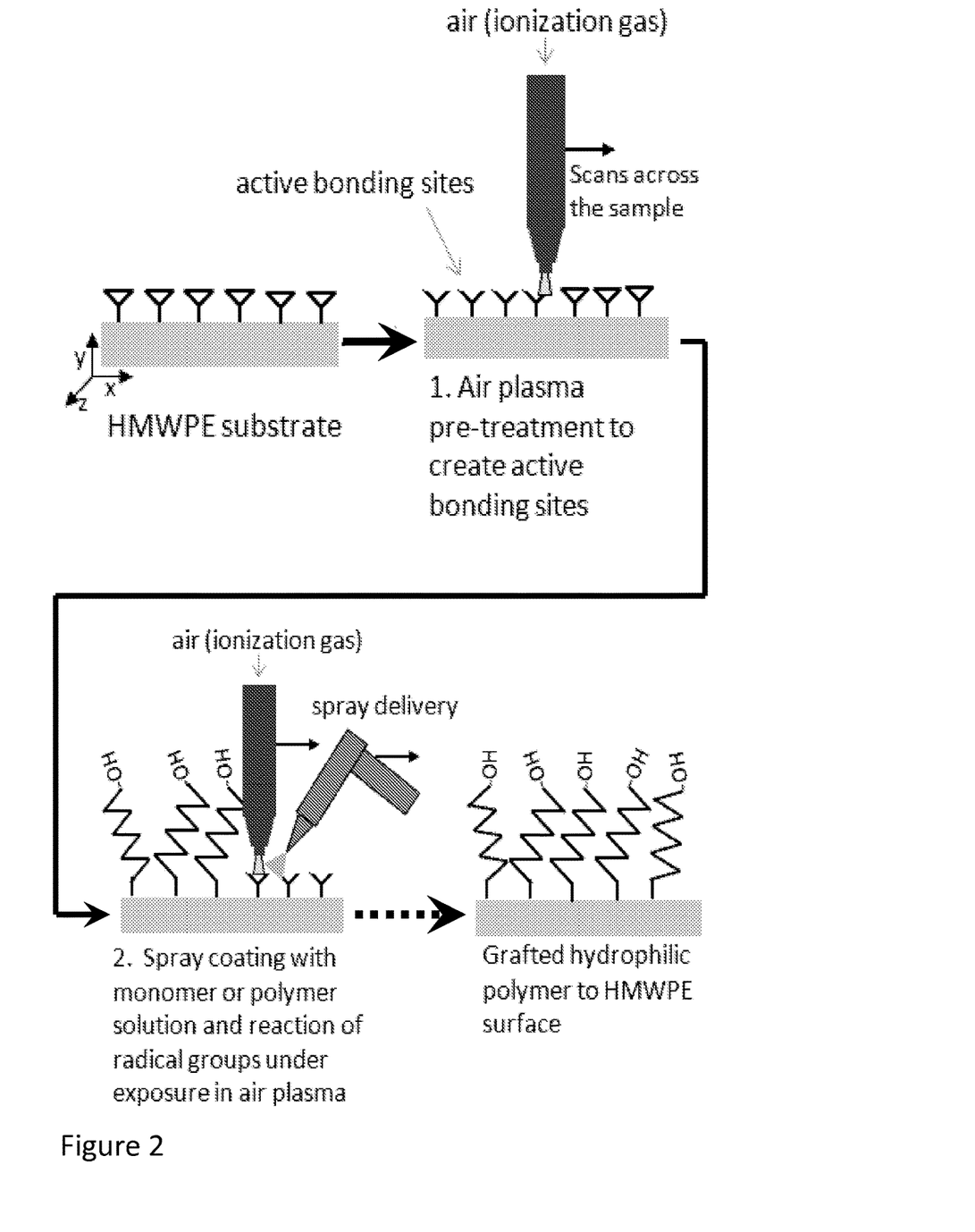
FIG. 2 is a schematic representation of a process or method used to graft biocompatible polymers to the substrate in one aspect of the invention.

Atmospheric pressure plasma is used to activate the surface of the article to create attractive or radical sites for bonding to the coating. Simultaneously, the plasma reacts with the chemical precursors to create a reactive site on the molecules and graft them to the surface of the article as well as cross-link the precursor molecules to form a coating, as shown in FIG. 2. The gas for the plasma may be any gas that can be ionized by a plasma generator that does not form a solid coating, such as nitrogen, oxygen, any noble gases, carbon dioxide, or any combination. The plasma may be generated by any plasma generator that can create a low temperature homogeneous plasma discharge in atmospheric conditions that is spatially separated from the plasma generation zone and electric field. The spatial separation of the chemical precursors from the plasma generation results in preservation of some features of the original molecule. This is particularly beneficial for materials with biocompatible or bioactive properties. The plasma can be powered using direct current (DC), pulsed-DC, radio frequency (RF), or microwave (MW) technology. One commercial example of such a plasma generator is the Openair® technology (Plasmatreat US LP, Elgin, Ill.). The plasma conditions, which are controllable and variable during the coating process, include the type of gas, energy parameters, the flow rate of gas, the distance from the substrate, and the rate of scanning. The optimum plasma conditions may differ for each combination of substrate, chemical precursor, and final application of the article. In general, the set of plasma conditions are tailored to meet the desired wear resistance, adhesion, durability, biocompatibility, hydrophilicity, and other desired properties of the applied coating.

According to another aspect of the present disclosure, a sub-layer may be applied to the surface of the article to provide additional functionality to the article. For example, a ceramic or tribological sub-layer may be applied to provide additional durability, resistance against wear, and/or physical barrier. The method of application of the sub-layer may include physical vapor deposition (PVD), chemical vapor deposition (CVD), or plasma enhanced chemical vapor deposition (PECVD). Alternatively, the method of application is atmospheric pressure plasma deposition.

According to yet another aspect of the present disclosure, the surface of the article, the surface of the sub-layer, or both surfaces are chemically modified using a pre-treatment process to increase chemical bonding of the surface to the coating. This surface pre-treatment method involve any process known to one skilled in the art including, but not limited to, plasma and/or corona treatment, chemical etching, priming with other chemicals, application of adhesive coatings, physical abrasion, or atmospheric pressure plasma exposure. Alternatively, the surface pre-treatment method involves exposing the surface of the article and/or sub-layer to atmospheric pressure plasma. The gas used for plasma pre-treatment may include any gas that does not form a solid coating from the plasma phase, including but not limited to, nitrogen, oxygen, water vapor, carbon dioxide, noble gas, or any combination of gases. The "desired" level of pre-treatment is that which will remove contaminants from the surface and create attractive or radical sites on the surface to increase bonding of the coating to the surface without damage to the article.

The following specific embodiments are given to illustrate the design of a wear resistant and biocompatible coating and a method of applying such a coating according to the teachings of the present disclosure and should not be construed to limit the scope of the disclosure. Those skilled-in-the-art, in light of the present disclosure, will appreciate that many changes can be made in the specific embodiments which are disclosed herein and still obtain alike or similar result without departing from or exceeding the spirit or scope of the disclosure. One skilled in the art will further understand that any properties reported herein represent properties that are routinely measured and can be obtained by multiple different methods. The methods described herein represent one such method and other methods may be utilized without exceeding the scope of the present disclosure.

Example 1

Polymer coatings made with biocompatible materials have been grafted onto high density polyethylene (HDPE) via atmospheric pressure plasma reacting with the chemical precursor. Example 1 involves poly(2-hydroxyethyl methacrylate) (pHEMA) and its monomer (HEMA), in which dilute, aqueous precursor solutions were applied to HMWPE substrates and atmospheric pressure plasma was used to graft the pHEMA and chemical reaction products of pHEMA, or alternatively used to polymerize the monomer (HEMA), on the substrate surface. General process description is shown in FIG. 2.

Figure 3:
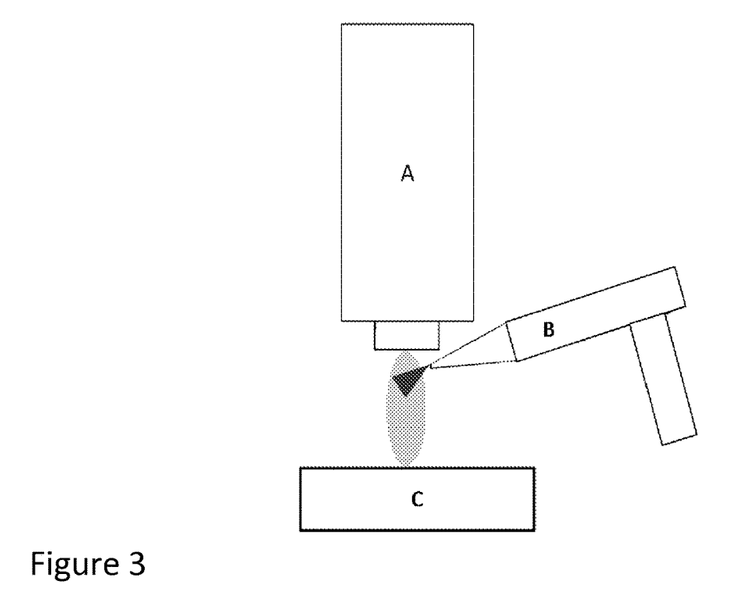
FIGS. 3 and 4 contain schematic representations of various apparatus configurations for coating a substrate according to the teachings of the present disclosure, in which the symbol 'A' denotes a plasma generator, the symbol 'B' denotes a chemical precursor, and 'C' denotes the substrate to be coated.
Figure 4:
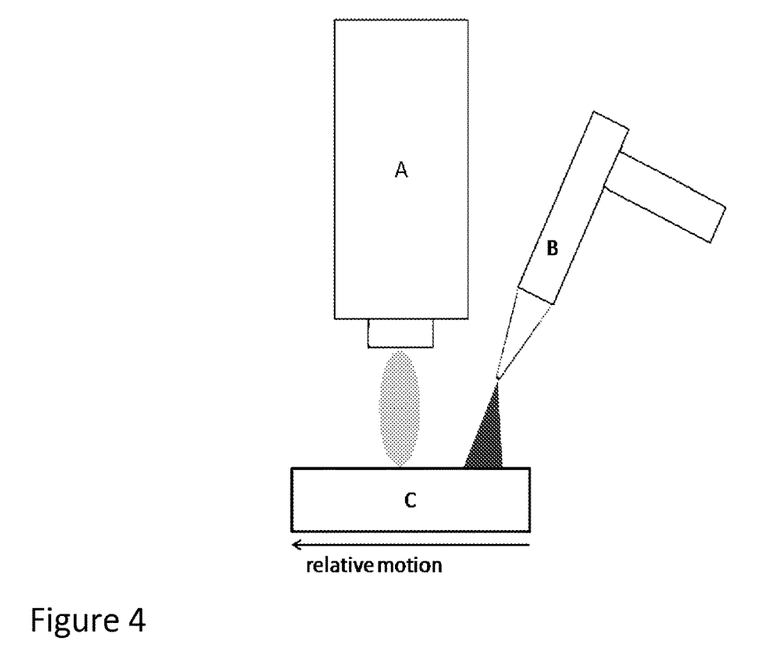

For some cases, the HMWPE substrate was first pre-treated by exposure to the plasma using air as the ionization gas. The purpose of the pretreatment was to activate the surface of the HDPE to allow for the pHEMA coating to bond to the active sites newly created on the surface. After pretreatment, the substrate was coated using the atmospheric pressure plasma coating process. The process involved spray application of the liquid precursor (the dilute pHEMA solutions or HEMA monomer) into the plasma stream using a carrier gas, as shown in FIG. 3, as well as spray application of the liquid precursor prior to plasma exposure, as shown in FIG. 4. Compressed dry air was used as the ionization gas for the plasma.

The process conditions were varied in order to understand their effects on the coating outcomes. The following lists the variables and ranges used for creating the coatings:

Plasma power (1.0-1.4 kW)
Scanning speed, which determines thickness (5-20 m/min)
Distance from plasma to substrate (1.5-2.5 cm)
Spray precursor delivery pressure, which determines flow rate (20-30 psig)

Pre-treatment with atmospheric plasma (applied/not applied)
Number of scans, where each scan is considered 1 coating layer (1-9)

Figure 5:
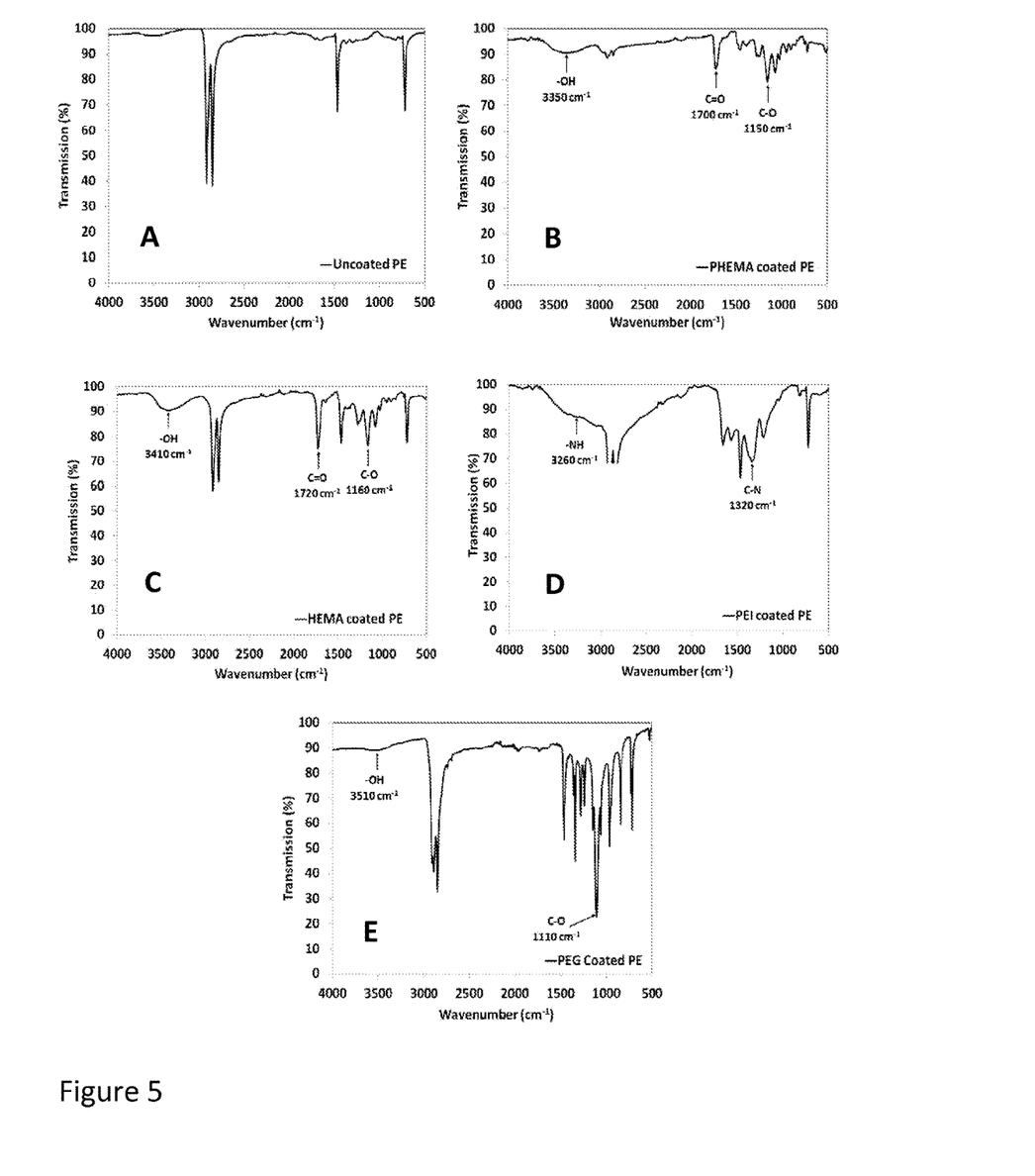
Figure 6:
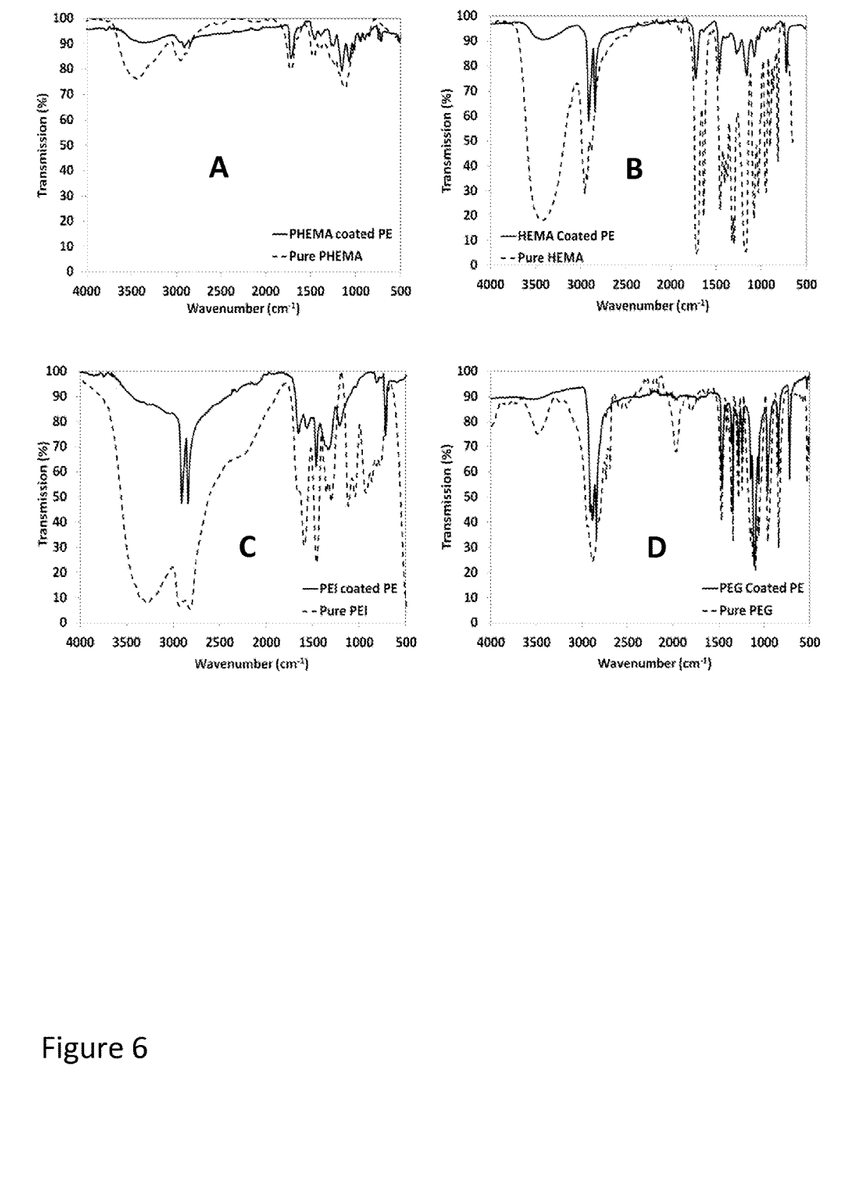

The coatings were analyzed using FTIR to evaluate chemical surface changes, contact angle to assess compatibility with aqueous fluid inside the body, and adhesion to determine the surface grafting strength and uniformity. FIG. 5 (a, b, and c) shows a sample FTIR measurement for pHEMA and HEMA grafted surfaces, as compared to untreated HMWPE. The FTIR results clearly show a significant chemical change on the surface of the HMWPE. Additionally, FIG. 6 shows a comparison FTIR of pure pHEMA solution and HEMA monomer as compared to a pHEMA and HEMA grafted HMWPE surface.

Figure 7:
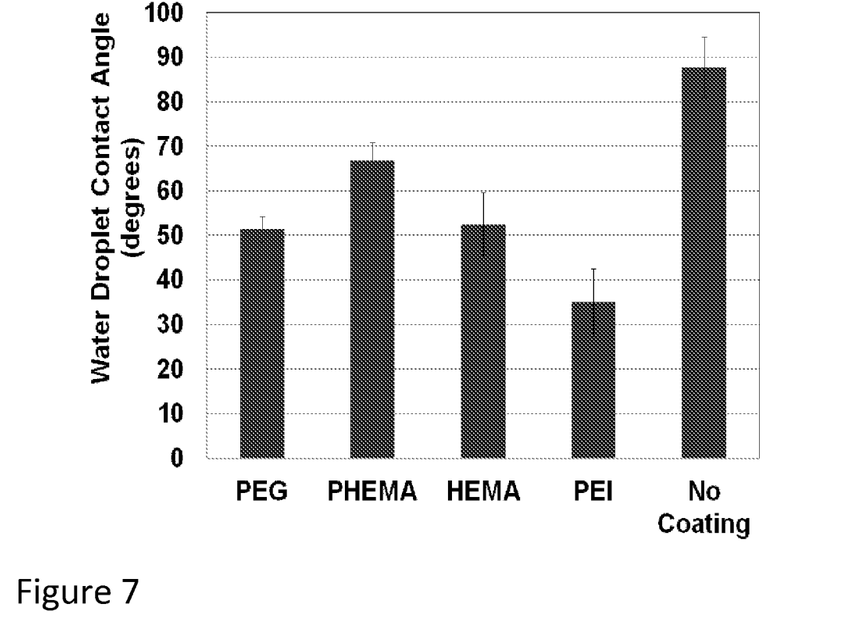
FIG. 7 is a graphical representation of contact angle measurements from untreated HMWPE and grafted surfaces, according to the teachings of the present disclosure.

Contact angle data using deionized (DI) water droplets were obtained for the samples plasma coated with pHEMA precursor solution and HEMA monomer. The water contact angle provides an indication of the hydrophilicity, as well as compatibility of the coatings with the internal aqueous body fluids. The effects of all of the factors were analyzed, with only the precursor delivery method as a significant factor. FIG. 7 shows the mean contact angle values of the untreated HMWPE and the plasma coated HMWPE samples. The results showed a significant decrease in contact angle for the samples with pHEMA plasma coating, indicating a significantly hydrophilic and water compatible surface.

Figure 8:
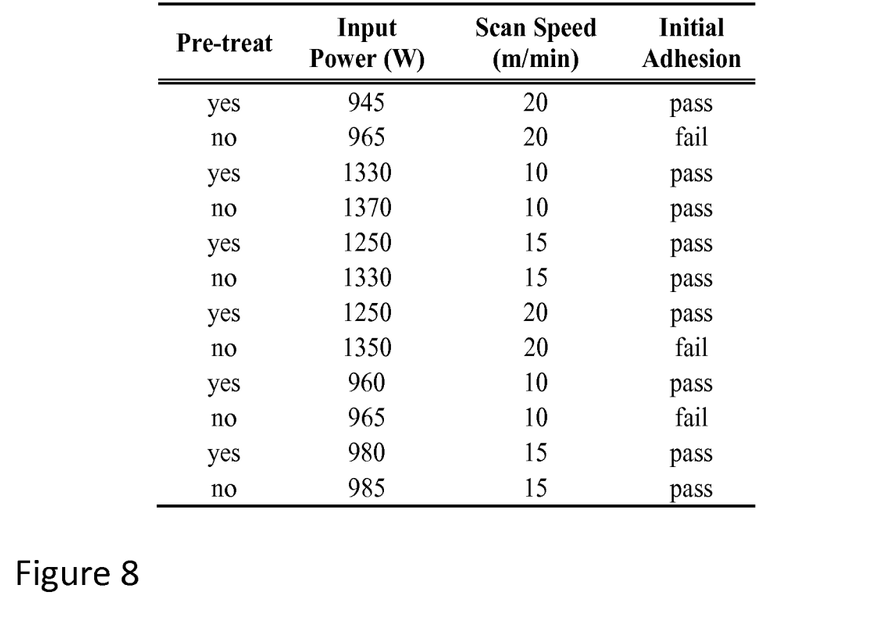
FIG. 8 is a table that shows adhesion testing results for the PHEMA and PEI grafted surfaces.

The adhesion testing was carried out using a tape test, ASTM D3359. A crosshatch pattern is marked on the sample using a blade tool, and a piece of tape is secured over the crosshatch and removed rapidly; the resulting crosshatch area is inspected and rated as either a pass or fail, along with the percentage of cross-hatch squares that failed. The samples pre-treated with plasma all passed adhesion, while those without plasma pre-treatment failed adhesion. Therefore, it can be said that the pre-treatment was necessary to promote bonding between the pHEMA precursor and the HMWPE substrate. FIG. 8 shows the results of the adhesion studies for pHEMA grafted surfaces.

Figure 9:
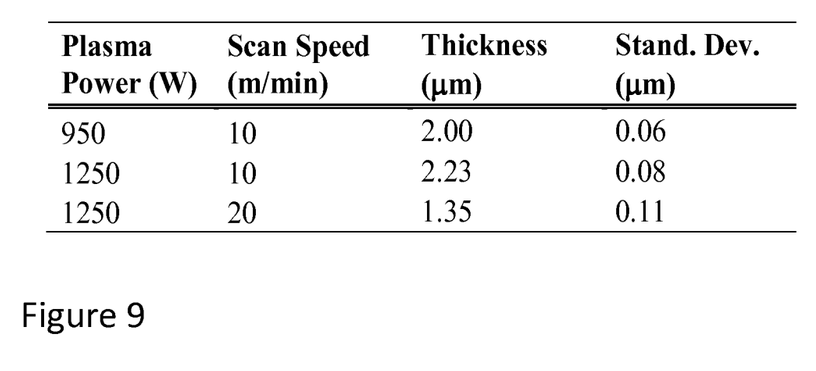
FIG. 9 is a table that compares thickness of grafted coatings for HEMA grafted to HMWPE substrates.

Grafted coatings of HEMA to HMWPE were analyzed for thickness and these results are shown in FIG. 9. Thicknesses were approximately 2 microns in some cases, significantly higher than previous results with other grafting methods, not including atmospheric pressure plasma.

Figure 10:
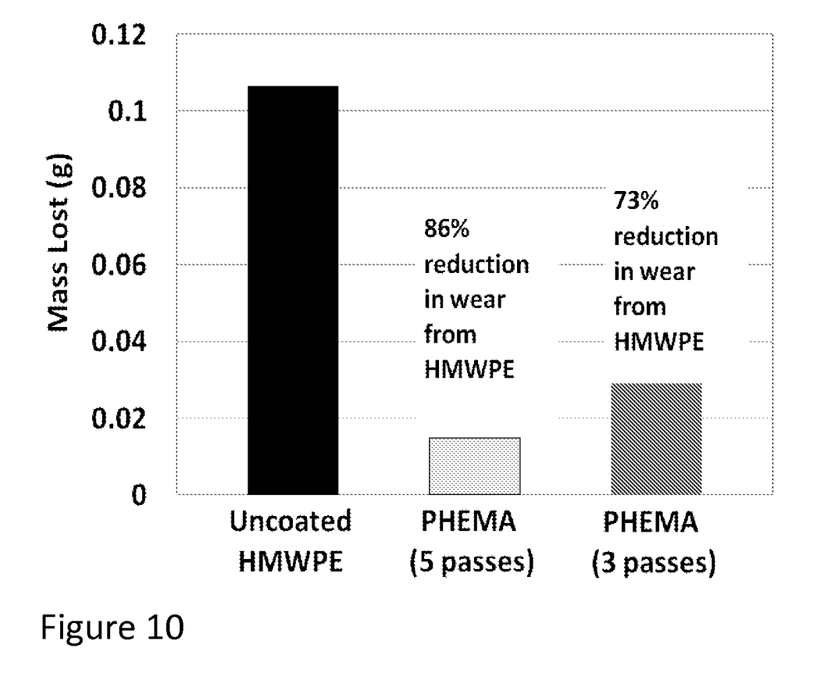
FIG. 10 is a graphical representation of the results of wear testing for PHEMA grafted surfaces as compared to the untreated HMWPE.

A stainless steel pin driven by an actuator made by Thomson Saginaw Ball Screw Company, LLC, Saginaw, Mich., was used as the primary device to conduct the wear experiments, to create a similar testing to a pin-on-disk wear test. The movement of the pin was random across the surface of the plaque. The mass of the semispherical pin (diameter 0.008 m) was 2.11 kg, resulting in a total contact pressure affecting the specimen equal to $4.12 \times 10^5$ N/m$^2$. Water was used to completely cover the test plaques during the wear testing. Wear tests were run over the course of one week for each sample, with average run times of 60 hours. Similar techniques have been used in literature. Results of preliminary wear testing are shown in FIG. 10 for both pHEMA grafted surfaces as compared to untreated HMWPE.

Cell proliferation studies using FKBP52 Knockout Mouse Embryonic Fibroblast (52KO MEF) cells were performed to analyze the biocompatibility of the PHEMA grafted surfaces. Preliminary findings after 6 days indicate no adverse effects on cell viability due to the plasma treatment.

Example 2

Example 2 involves aqueous solutions of polyethylinemine (PEI) as chemical pre-cursor applied to HDPE substrates and atmospheric pressure plasma was used to graft the PEI and chemical reaction products of PEI to the substrate and cure the coatings. Refer to FIGS. 2-4 for methods of grafting. The following process conditions were varied for analysis of their effects:

Concentration of precursor solution (4-16 wt % PEI in DI water)
Plasma power (0.9-1.4 kW)
Scanning speed, which determines thickness (10-20 m/min)
Pre-treatment with atmospheric plasma (applied/not applied)
Number of scans, where each scan is considered 1 coating layer (1-9)

FIG. 5 shows the FTIR results for PEI plasma coating and untreated HDPE. These samples were generated by pre-application of precursor with a spray gun mounted onto the moving plasma jet spraying the samples before plasma exposure, as shown in FIG. 3. As seen in this chart, the broad —OH peak is apparent at 3300 $cm^{-1}$ and the PEI plasma coating significantly modified the surface chemistry. Additionally, FIG. 6 shows the FTIR comparison for pure PEI as compared to the PEI grafted HMWPE.

In addition to FTIR, contact angle analysis was performed for PEI samples to assess the compatibility of the surfaces with aqueous solution as in the body. Contact angle measurements were obtained using DI water and albumin, which represents a similar make-up as body fluid. The results in FIG. 7 show that the coatings were significantly hydrophilic.

Figure 11:
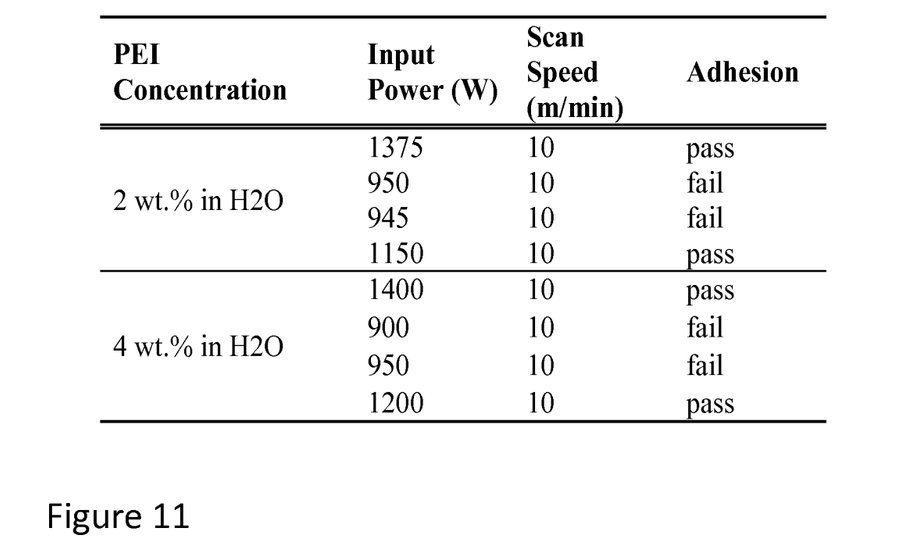
FIG. 11 is another table that shows adhesion testing results for the PHEMA and PEI grafted surfaces.

The adhesion testing was carried out using a tape test, ASTM D3359, as described in the previous example. As in the previous example, plasma pre-treatment was necessary pass the adhesion test and to promote better bonding between the liquid precursor and the HDPE substrate. In some cases, coatings failed adhesion due to the inadequate plasma power to dissociate the bonds for proper grafting. FIG. 11 shows the results of the PEI grafted surfaces adhesion testing.

Example 3

The third example included aqueous solutions of 25 wt % polyethylene glycol (PEG) as a chemical pre-cursor that was applied to HDPE substrates. Atmospheric pressure plasma was used to graft the PEG and chemical reaction products of PEG to the substrate and cure the coatings. The following process conditions were varied for analysis of their effects:

Plasma power (0.9-1.3 kW)
Number of scans, where each scan is considered 1 coating layer (1, 3)
Pre-treatment with atmospheric plasma (applied/not applied)

FIGS. 5 and 6 show the FTIR results for PEG plasma coating and untreated HMWPE. The PEG plasma coated samples were generated by pre-application of precursor with a spray gun mounted onto the moving plasma jet spraying the samples before plasma exposure, as shown in FIG. 3. As seen in this chart, PEG plasma coating significantly modified the surface chemistry.

Contact angle analysis was performed for PEG samples to assess the compatibility of the surfaces with aqueous solution as in the body. Contact angle measurements were obtained using DI water. The results in FIG. 7 show that the coatings were significantly hydrophilic, indicating compatibility with aqueous solutions, such as in the body.

Example 4

The fourth example includes the addition of a highly abrasion resistant coating as sublayers underneath the plasma coatings made with poly(vinyl alcohol) (PVA) in aqueous solution as a precursor. The abrasion resistant layer was created by depositing organosilicon coating via atmospheric pressure plasma deposition. Dilute, aqueous precursor solutions (<1.5 wt. % of PVA) were applied to HDPE substrates that had been coated with the organosilicon layer, and atmospheric pressure plasma was used to graft the precursor and the chemical products to the substrate and cure the coatings.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of forming a biocompatible or biologically inert article for use in an application in which the article will make contact with at least one tissue, organ, or fluid within a human or animal body; the method comprising the steps of:
   providing an article having an external surface;
   selecting chemical precursors;
   directing one or more chemical precursors towards the external surface or directly applying such chemical precursors to the external surface;
   activating the chemical precursors by exposing said precursors to atmospheric pressure plasma; and
   grafting and/or cross-linking the activated chemical precursors to form a solid biocompatible coating adjacent to the external surface of the article;
   wherein the chemical precursors include polymethacrylates, polyacrylates, polyurethanes, polyethylene, polyanhydrides, polyesters, polyglycolic acid, polylactic acids, polycaprolactone, polyketones, polyhydroxyethylmethacrylate (PHEMA), polyethylenimine (PEI), polyvinyl alcohol, polyethylene glycol, polyvinyl pyrolidone, or any polymer approved by the Federal Drug Administration (FDA) for use in the human body,
   wherein the biocompatible coating increases the wear resistance of the external surface in a pin-on-disk wear test.

2. The method according to claim 1, wherein the method further comprises the step of applying a sub-layer to the external surface of the article or pre-treating the external surface prior to the application of the solid coating; the sub-layer or the pretreatment capable of enhancing adhesion of the solid coating to the article, providing additional wear or abrasion resistance, or increasing hardness of the coating.

3. The method according to claim 2, wherein the pretreatment of the external surface is accomplished using plasma or corona treatment, chemical etching, chemical priming, physical abrasion, or applying an adhesive film.

4. The method according to claim 2, wherein the sub-layer is applied using physical vapor deposition, chemical vapor deposition, atmospheric plasma deposition, plasma enhanced chemical vapor deposition, or atmospheric pressure plasma deposition.

5. The method according to claim 1, wherein the article is a medical device or a biomedical implant having a body constructed from a metal, a ceramic, a plastic, or a combination thereof.

6. The method according to claim 1, wherein the chemical precursors further includes monomers, small molecules, or mixtures thereof, based upon their ability to exhibit biocompatibility or biological inertness.

7. The method according to claim 1, wherein the means of directing the chemical precursors towards or applying the chemical precursors to the external surface selected from the group consisting of dip coating, flow coating, spin coating, spray or atomization coating, and a combination thereof.

8. The method according to claim 1, wherein the chemical precursors are dissolved in a solution of water, monomer, solvent, or combination thereof.

9. The method according to claim 1, wherein the means of directing the chemical precursors towards the surface of the article includes injecting or drawing the precursors into a flow of a carrier gas; the carrier gas being nitrogen, oxygen, noble gases, carbon dioxide, or a combination thereof.

10. The method according to claim 9, wherein the means of directing the chemical precursors towards the article's surface is controlled using the flow rate of the chemical precursors, the flow rate of the carrier gas, and the location of the flow exit approximate the surface.

11. The method according to claim 1, wherein the activating the chemical precursors by exposure to atmospheric pressure is accomplished by creating the atmospheric pressure plasma using a plasma source selected from the group consisting of a Dielectric Barrier Discharge (DBD) system, a microwave plasma system, a hollow cathode system, a plasma jet, and a plasma array.

12. The method according to claim 1, wherein the plasma is created using a plasma generator using direct current, radio frequency, or microwave technology.

* * * * *